US009637587B2

(12) United States Patent
Stepanski et al.

(10) Patent No.: US 9,637,587 B2
(45) Date of Patent: May 2, 2017

(54) METHOD FOR THE MANUFACTURE OF A POLYHYDROXY-CARBOXYLIC ACID

(75) Inventors: Manfred Stepanski, Buchs (CH); Francois Loviat, Sennhof (CH); Andrzej Kuszlik, Buchs (CH)

(73) Assignee: Sulzer Chemtech AG, Winterthur (CH)

( * ) Notice: Subject to any disclaimer, the term of this patent is extended or adjusted under 35 U.S.C. 154(b) by 41 days.

(21) Appl. No.: 13/985,770

(22) PCT Filed: Nov. 15, 2011

(86) PCT No.: PCT/EP2011/070168
§ 371 (c)(1),
(2), (4) Date: Aug. 15, 2013

(87) PCT Pub. No.: WO2012/110117
PCT Pub. Date: Aug. 23, 2012

(65) Prior Publication Data
US 2013/0324697 A1    Dec. 5, 2013

(30) Foreign Application Priority Data

Feb. 18, 2011 (EP) .................................. 11154929
Feb. 18, 2011 (EP) .................................. 11154930
Nov. 2, 2011 (EP) .................................. 11187571
Nov. 2, 2011 (EP) .................................. 11187572

(51) Int. Cl.
*C08G 63/08* (2006.01)
*B01D 9/00* (2006.01)
*B01D 19/00* (2006.01)
*C07D 319/12* (2006.01)
*C08G 63/90* (2006.01)
*B01D 3/10* (2006.01)
*C08G 63/78* (2006.01)
*C08F 124/00* (2006.01)
*C08L 67/04* (2006.01)

(52) U.S. Cl.
CPC .............. *C08G 63/08* (2013.01); *B01D 3/10* (2013.01); *B01D 9/0013* (2013.01); *B01D 9/0045* (2013.01); *B01D 19/0036* (2013.01); *C07D 319/12* (2013.01); *C08G 63/78* (2013.01); *C08G 63/785* (2013.01); *C08G 63/90* (2013.01); *C08F 124/00* (2013.01); *C08L 67/04* (2013.01)

(58) Field of Classification Search
CPC ....... C08L 67/04; C08F 124/00; C08G 63/08; C08G 63/90; C08G 63/78
See application file for complete search history.

(56) References Cited

U.S. PATENT DOCUMENTS 3,621,664 A    11/1971 Saxer
4,057,537 A    11/1977 Sinclair 5,142,023 A    8/1992 Gruber et al.
5,357,034 A *  10/1994 Fridman et al. .............. 528/354
5,521,278 A    5/1996 O'Brien et al.
5,728,847 A    3/1998 Ohara et al.
5,770,682 A    6/1998 Ohara et al.
5,801,255 A    9/1998 Ohara et al.
5,866,677 A    2/1999 Maeda et al.
5,880,254 A    3/1999 Ohara et al.
6,187,901 B1   2/2001 Koskinen et al.
6,241,954 B1   6/2001 Jansen et al.
6,313,319 B1 * 11/2001 Ohara ..................... A23C 11/06
                                                              426/133

(Continued)

FOREIGN PATENT DOCUMENTS

| EP | 0 261 572 A1 | 9/1987 |
| EP | 0 324 245 A2 | 12/1988 |
| EP | 0 728 508 A1 | 2/1995 |
| EP | 0 755 956 A2 | 1/1997 |
| EP | 0 891 798 A1 | 7/1997 |
| EP | 1 092 459 A1 | 10/2000 |
| EP | 1 245 951 A1 | 3/2002 |
| JP | 56-4688 | 1/1981 |
| JP | 59-096123 | 6/1984 |
| JP | 07-033861 | 2/1995 |
| JP | 2822906 | 8/1996 |
| JP | 10-101777 | 4/1998 |
| JP | 11217425 | 8/1999 |
| RU | 2008116595 A | 11/2009 |
| RU | 2404198 C2 | 11/2010 |
| WO | 2009121830 A1 | 10/2009 |

OTHER PUBLICATIONS

Stepanski, Manfred et al. "Purification of Dilactide through Melt Crystallization, Soda Cups Made of Sugar", Sulzer Technical Review, Jan. 1, 2008, pp. 8-11, retrieved from http://www.sulzer.com/en/-/media/Documents/Cross_Division/STR/2008/2008_1_8_stepanski_e.pdf.

*Primary Examiner* — Gregory Listvoyb
(74) *Attorney, Agent, or Firm* — Larson & Anderson, LLC

(57) ABSTRACT

Disclosed is a method to prepare a polylactic acid comprising the steps of performing a ring opening polymerization using a catalyst and either a catalyst killer compound or an endcapping additive to obtain a raw polylactic acid of MW greater than 10,000 g/mol, purifying the raw polylactic acid by removing and separating low boiling compounds comprising lactide and impurities from the raw polylactic acid by devolatization of the low boiling compounds as a gas phase stream, and purifying the lactide from the devolatization and removing the impurities from the gas phase stream of evaporated low boiling compounds by means of crystallization by desublimation from the gas phase, wherein the lactide is purified and the removed impurities include a catalyst residue and a compound containing at least one hydroxyl group such that the purified lactide is then polymerized by feeding it back into the ring opening polymerization. The invention further relates to an apparatus for carrying out the method comprising a polymerization reactor for performing a ring opening polymerization to obtain a raw polylactic acid, a devolatization apparatus for separating low boiling compounds comprising lactide and impurities from a raw polylactic acid, and a crystallization apparatus for purifying a lactide and removing impurities by means of a desublimation and a crystallization in the same crystallization apparatus.

15 Claims, 10 Drawing Sheets

(56) References Cited

U.S. PATENT DOCUMENTS

| | | |
|---|---|---|
| 6,467,305 B1 | 10/2002 | Roodenrijs et al. |
| 6,719,954 B2 | 4/2004 | Jansen |
| 7,179,435 B2 | 2/2007 | Ruemekorf et al. |
| 7,488,783 B2 | 2/2009 | Coszach et al. |
| 2006/0014975 A1* | 1/2006 | Coszach ................ C08G 63/08 560/179 |
| 2009/0036600 A1 | 2/2009 | Sodergard et al. |
| 2010/0099893 A1 | 4/2010 | Scholz et al. |

* cited by examiner

METHOD FOR THE MANUFACTURE OF A POLYHYDROXY-CARBOXYLIC ACID

This invention relates to a method for the manufacture of a polyhydroxy-carboxylic acid, in particular a polylactic acid in which the yield is increased with respect to the final product by recycling of the lactide from a side stream stemming from the purification of raw polylactic acid and the recycling of the lactide obtained resulting from this purification. Furthermore the invention relates to an apparatus for carrying out the method to produce a polylactic acid. The invention also relates to a method for a melt layer crystallization of a vaporous biodegradable, intermolecular cyclic diester of an alpha-hydroxy-carboxylic acid.

Polylactic acid, which will be also referred to as PLA in the subsequent text, is a biodegradable polymer, which is synthesized from lactic acid. A particular advantage of such polymers is their biocompatibility. By the term biocompatibility, it is meant that they only have a very limited negative influence on any living creatures in the environment. A further advantage is that polylactide polymers are derived from an entirely renewable raw material, such as e.g. starch and other saccharides coming from e.g. sugar cane, sugar bets and the like.

Polylactide polymers have been increasingly commercialized already since mid of 20$^{th}$ century. However, mainly due to restricted monomer availability and high manufacturing costs, their original use was mainly in the medical sector, such as chirurgical implants or surgical sutures, e.g. nails, screws, sewing material or reinforcing material for bone fractures. An interesting property of the PLA is the decomposition of the polylactide polymers in the body saving a second surgical treatment for removing any implant. Furthermore, PLA can be used in sustained release capsules for the controlled dispensing of drugs.

In the recent decades, due to strongly increasing crude oil prices and environmental awareness along with improvements of production methods, making the polylactide polymers became more interesting for packaging in particular of food, both as stiff packaging as well as flexible foils, such as mono-axially or bi-axially stretched films. Other applications are fibers, e.g. for textiles used in garments, furniture upholstery or carpets. Furthermore, extrusion products like one-way cutlery or containers, for office supplies or hygienic articles. The polylactide polymers can also be combined with other materials to form composite materials.

Currently, two production methods are known to PLA manufacture.

The first of these production methods includes the direct polycondensation of lactic acid to polylactic acid, as described in JP733861 or JP5996123. A solvent is used in addition to the lactic acid for performing the polycondensation reaction. Furthermore, water has to be discharged continuously during the entire polycondensation process in order to allow for the formation of polylactide polymers of high molecular weight. For all these reasons, this method has not been commercialized.

The method that has been established for commercial PLA manufacture uses the intermediate product lactide to initiate a subsequent ring opening polymerization leading from the lactide to polylactic acid. A number of variants to this methods have been disclosed e.g. in U.S. Pat. No. 5,142,023, U.S. Pat. No. 4,057,537, U.S. Pat. No. 5,521,278, EP261572 JP564688B, JP2822906, EP0324245, WO2009121830.

The methods described in these documents have the following main steps in common:

In a first step, the raw material is processed, e.g. starch, or other saccharides extracted e.g. from sugar cane or beets, corn, wheat; in a second step a fermentation using suitable bacteria to obtain lactic acid is performed; in a third step the solvent—typically water—is removed from the mixture to prevent negative effects of the solvents in the subsequent steps. In a fourth step the lactic acid is catalytically dimerized to form raw lactide. Typically, an optional intermediate step is performed, which includes pre-polymerization of the lactic acid to low molecular weight polylactic acid and subsequent de-polymerization to form raw lactide. A fifth step includes purification of the lactide to remove foreign substances, which may influence the polymerization in a negative manner and contribute to the coloring as well as the odor of the final product. The separation can either be performed by distillation or by crystallization. In a sixth step, a ring opening polymerization for obtaining raw polylactic acid of high molecular weight is obtained. The molar mass is approximately 20000 to 500000 g/mol according to U.S. Pat. No. 6,187,901.

Optionally, copolymerization compounds can be added during the ring opening polymerization. In a seventh step, the raw polylactic acid is purified to obtain a purified polylactic acid. In this stage, low boiling compounds are removed, which would decrease the polymer stability and would in a negative way influence the parameters of subsequent plastics manufacture, like viscosity or rheological properties of the molten polymer, and which would contribute to the coloring and unwanted odors of the final product. According to U.S. Pat. No. 5,880,254, the raw polylactic acid may be solidified to form granulate, which is contacted with a tempered inert gas flow e.g. in a fluid bed. The lowest boiling compounds of the raw polylactic acid are carried away by the inert gas. Yet another method is described in U.S. Pat. No. 6,187,901. According to this method, the liquid raw polylactic acid is sprayed by a plurality of nozzles so as to form a plurality of liquid threads. The inert gas passes around the liquid threads and the lactide evaporates into the hot inert gas flow. The flow of low boiling compounds typically contains up to 5% weight of dilactide.

The lactic acid has two enantiomers, L-lactic acid and D-lactic acid. Chemically synthesized lactic acid contains the L-lactide and D-Lactide in the racemic mixture of 50% of each of the enantiomers. However, the fermentation process is made more selective by using appropriate microbe cultures to selectively obtain L- or D-lactic acid.

The lactide molecules which are produced by the dimerization of the lactic acid appear in three different forms: L-L-lactide, which is also called L-lactide, D-D-lactide, which is also called D-lactide and L, D-lactide (or D, L lactide), which is called meso-lactide. L and D-lactides are optically active, whereas meso-lactide is not. The purification steps for purifying raw lactide typically include a separation of a stream rich in L-lactide and a stream rich in D-lactide and a further stream rich in meso-lactides, each of which can be purified separately. By blending at least two of the three lactide forms, the mechanical properties and the melting point of the polymers formed by the polylactic acid can be influenced. For example, by admixing appropriate amounts of one enantiomer to the other, the crystallization rate of the polymer is decreased, that in turn allows foaming of the manufactured plastic mass without being obstructed by too rapid solidification.

Attempts have been made to increase the yield of the polylactic acid process and to reduce manufacturing costs for polylactic acid.

U.S. Pat. No. 5,142,023 teaches that the gaseous stream of the low boiling compounds of the purification step of the raw lactide are fed at least partially back into the lactide reactor. A heavy residue forms in the lactide reactor, which can be partially bypassed back into the reactor itself or fed back into the separation device for separating the solvent from the lactic acid after fermentation.

U.S. Pat. No. 7,488,783 teaches that raw lactide is crystallized to form a purified lactide. A second crystallization step is performed onto the residue of the first crystallization step to separate the lactide therefrom. This lactide is fed back to the first crystallization step or to one of the previous process steps according to the method.

U.S. Pat. No. 5,521,278 teaches that the raw lactide is crystallized. The residue flow is evaporated, condensed selectively and recycled back to one of the previous process steps according to the method.

JP2822906 discloses the solidification of a gaseous raw lactide stream to pure lactide. The residue, which is not solidified is recycled back into the lactide reactor.

JP10101777 discloses that the gaseous raw lactide stream is solidified partially by a cooling inert gas stream to form pure lactide The residue is fed back into the lactide reactor. This raw lactide stream stems from a direct polycondensation reaction. This raw lactide stream is gaseous. By cooling the raw lactide stream generated by said polycondensation reaction to a temperature in which the lactide crystallizes in a crystallization flowing-back equipment with a self cleaning function. This crystallization flowing-back equipment has a rotary driving means for rotating two screws arranged in a cylinder, whereby the rotating screws are disposed with intermeshing gears. The cylinder is cooled by a cooling medium circulating in a cooling jacket arranged in the cylinder wall to the temperature in which a part of the low molecular weight compound of lactide and lactic acid crystallizes and is conveyed towards the vent-port by the two screws and flows back from this vent-port to the batch process polycondensation reactor. The crystallization is performed by using a solvent. Such a solvent, e.g. water is used to lower the viscosity of the melt, which is believed to improve the mass transfer. Therefore the low melting compounds separate more readily from the high melting compounds, which form a crystal fraction on the crystallization surface of the crystallization apparatus. Thus a contamination of the crystals is believed to be reduced if the viscosity of the melt is reduced. The object of the invention as disclosed in JP10101777 is to remove the solvent.

Any of the described methods concern a recycle of partial stream from the raw lactide purification. Any of these methods serves to increase the yield of the method, however do not disclose if the lactide can be recycled which is still present in the raw polylactic acid at a percentage of up to 5%.

Document U.S. Pat. No. 6,187,901 relates to a method for the removal of lactide from polylactide and the recovery of lactide from a lactide-containing gas. The raw polylactic acid is sprayed into a space containing a hot inert gas by means of spray nozzles. Thereby thin threads are formed. These threads fall under gravity and under laminar flow conditions. Thereby the polymer melt flows more rapidly into the inner parts of the thread than in the surface part. Thereby the polymer melt flowing in the inner part of a sufficiently thin thread forms a new material transfer surface for lactide evaporation during its downward path. The lactide evaporates partially and is collected in the inert gas, from which it crystallizes in a crystallization chamber by rapid cooling. The crystals obtained are separated in a cyclone or filter device and recycled into the polymerization reactor. The amount of lactides in the polylactic acid can be reduced by this process step up to 1%. However, the lactide recycling requires an inert gas flow, which has to be cleaned before discharge as a waste stream.

Document U.S. Pat. No. 5,880,254 discloses a method for producing polylactic acid. The raw polylactic acid is crystallized in the form of granulate. The granulate is subjected to a hot inert gas flow passing through the granulate forming a fluid bed. The lactide contained in the granulate is evaporated and carried away with the inert gas flow and fed back into the polymerization reactor. The purified polylactic acid contains still about 1% of dilactide.

Each of the methods of U.S. Pat. No. 6,187,901 or U.S. Pat. No. 5,880,254 require an inert gas, which has to be treated for recycling that in turn requires additional equipment having the consequence of increased costs for the purification of the polylactic acid.

SUMMARY OF THE INVENTION

An object of the invention is to provide an improved method for preparing a polylactic acid not having the disadvantages of the earlier discussed methods, and a further object is to reduce the equipment needed for treatment of the inert gas and to increase the yield compared to the methods according to U.S. Pat. No. 6,187,901 or U.S. Pat. No. 5,880,254.

According to the invention, the first object is achieved by a method to prepare a polylactic acid comprising the steps of performing a ring opening polymerization using a catalyst and either a catalyst killer compound or an endcapping additive to obtain a raw polylactic acid of MW greater than 10,000 g/mol, purifying the raw polylactic acid by removing and separating low boiling compounds comprising lactide and impurities from the raw polylactic acid by devolatization of the low boiling compounds as a gas phase stream, and purifying the lactide from the devolatization and removing the impurities from the gas phase stream of evaporated low boiling compounds by means of crystallization by desublimation from the gas phase, wherein the lactide is purified and the removed impurities include a catalyst residue and a compound containing at least one hydroxyl group such that the purified lactide is then polymerized by feeding it back into the ring opening polymerization.

The further object is achieved by an apparatus for carrying out the method comprising a polymerization reactor for performing a ring opening polymerization to obtain a raw polylactic acid, a devolatization apparatus for separating low boiling compounds comprising lactide and impurities from a raw polylactic acid, and a crystallization apparatus for purifying a lactide and removing impurities by means of a desublimation and a crystallization in the same crystallization apparatus.

In a preferred embodiment of the method, the desublimation occurs on a cooled surface. In another preferred embodiment of the method, an apparatus for the crystallization and an apparatus for the devolatization operate substantially under a same vacuum condition. In yet another preferred embodiment, the desublimation and the crystallization occur in a same apparatus. In still yet another preferred embodiment, the apparatus for the crystallization has no inert gas stream. In still yet another preferred embodiment, the evaporated gas phase stream from the devolatization contains at least 30% of lactide, preferably at least 60%, most preferred at least 90%. In still yet another preferred embodiment, the lactide is first subjected to a sweating step, followed by a melting step, prior to feeding it back into the ring opening polymerization. In still yet another preferred embodiment, the devolatization operates under a lactide partial pressure of less than 20 mbar, preferably less than 10 mbar, particularly preferred less than 5 mbar. In still yet another preferred embodiment, the removed impurities include either an organometallic compound or a carboxylic acid. In still yet another preferred embodiment, at least a portion of a purge stream from the crystallization is recycled to a raw lactide purification step, a pre-polymerization and dimerization step, or a solvent removal step in the production of a purified lactide. In still yet another preferred embodiment, a liquid from the sweating step is collected and recrystallized in order to recover the lactide.

In a preferred embodiment of the apparatus of the invention, no throttling means or vacuum pumps are arranged between the crystallization apparatus and the devolatization apparatus. In another preferred embodiment, a heat exchanger is arranged between the devolatization apparatus and the crystallization apparatus. In yet another preferred embodiment, the crystallization apparatus has heat exchanging surfaces for the solidification of a gaseous stream.

DETAILED DESCRIPTION OF THE INVENTION

An object of the invention is a method comprising purification of polymerizable monomers or oligomers like lactide by crystallization, in which in a first step, a ring opening polymerization for obtaining raw polylactic acid of high molecular weight of greater than 10 000 g/mol is performed;

in a second step, the raw polylactic acid is purified to obtain a purified polylactic acid whereby during the second step, low boiling compounds are removed and the separation of the low boiling compounds from the raw polylactic acid is achieved by devolatization and in a third step, the lactide is recycled and impurities are removed from the evaporated gas phase stream of the second step by means of crystallization or solidification from the gas phase. During the third step, the impurities are removed such that the purified lactide can be added again to the ring opening polymerization of the second step. Such impurities can comprise coloring and odor generating compounds or any additive byproduct, such as water, catalyst residues, e.g. organometallic compounds, reaction byproducts, compounds containing at least one hydroxyl-group (—OH), acidic compounds, such as carboxylic acids, catalyst killer compounds or endcapping additives.

Advantageously the molecular weight of the raw polylactic acid is at least 10 000 g/mol, preferably at least 15 000 g/mol, particularly preferred at least 20 000 g/mol. Optionally other polymerizable monomers or oligomers can be included, such as at least one of the group of a glycolactide copolymer, a polyglycolic acid or polyglycolide acid (PGA), a block copolymer a styrene-butadiene-methacrylate (SBM) copolymer of polystyrene, 1,4-polybutadiene, a syndiotactic poly methyl methacrylate (PMMA), a triblock copolymer with a center block of poly butyl acrylate surrounded by two blocks of poly methyl methacrylate, poly methyl methacrylate (PMMA), polyether ether ketone (PEEK), polyethylene oxide (PEO), polyethylene glycol (PEG), polycaprolactam, polycaprolactone, polyhydroxybutyrate.

Typical comonomers for lactic acid or lactide copolymerization are glycolic acid or glycolide (GA), ethylene glycol (EG), ethylene oxide (E0), propylene oxide (PO), (R)-β-butyrolactone (BL), δ-valerolactone (VL), ε-caprolactone, 1,5-doxepan-2-one (DXO), trimethylene carbonate (TMC), N-isopropylacrylamide (NIPAAm).

The raw polylactic acid may also contain further impurities.

At the end of polymerization the temperature dependent equilibrium between the monomer and the polymer is reached, whereby the raw polylactic acid contains about 5 weight % of non-reacted lactide. The monomer content has to be reduced to less than 0.5 weight % in order to obtain the required mechanical, chemical, rheologic and thermal properties of the polymer for further processing thereof.

The evaporated gas phase stream leaving the devolatization can be condensed, whereby a condensed stream is obtained. The evaporated gas phase stream contains at least 30% of lactide by weight. The impurities should be present only in small amounts, thus water should be at most 10 ppm, preferably 5 ppm, particularly preferred less than 0.5 ppm. Any lactic acid in the evaporated gas phase stream should be below 100 mmol/kg, preferably less than 50 mmol/kg, particularly preferred less than 10 mmol/kg. The condensed stream is crystallized from its liquid state and the crystallization is advantageously performed without solvent. This has the particular advantage, that further steps to remove any solvents are not required. Advantageously, the crystallization step is performed in one of a melt layer crystallization apparatus or a desublimation apparatus, such as at least one of a falling film crystallizing apparatus or a static crystallization apparatus, or a suspension crystallization, which is performed in at least one suspension crystallization apparatus. If a suspension crystallization apparatus is used, the condensed stream is cooled so as to form lactide crystals floating freely in the liquid phase of the suspension crystallization apparatus, thereby forming a partially crystallized liquid stream, which is subsequently fed into a wash apparatus.

As an alternative, the evaporated gas phase stream can be desublimized, thus cooled from the gas phase directly to the solid phase in a desublimation step.

The crystal fraction obtained by the crystallization according any of the alternatives outlined above contains the purified lactide. Advantageously the devolatization operates under a lactide partial pressure of less than 20 mbar, preferably less than 10 mbar, particularly preferred less than 5 mbar. The solidified fraction containing purified lactide may be melted in a subsequent heating step to be fed back into the ring opening polymerization. A sweating step can be performed before the heating step for the solidified fraction present in crystalline form on the crystallization surfaces. The mother liquor can remain between the crystal and thereby form inclusions containing impurities. During the sweating step, these impurities are removed.

The evaporated gas phase stream from the devolatization contains at least 30% of lactide, advantageously at least 60% of lactide, most preferred at least 90% of lactide. For increasing the yield of the lactide from the evaporated gas phase stream, the mother liquor and/or liquid from sweating stage can be fed into a recrystallization stage.

According to a preferred embodiment of the invention, the crystallization apparatus is connected directly to the devolatization apparatus by means of a gas line or optionally a heat exchanger arranged between the devolatization and the crystallization. The heat exchanger is configured in particular as a gas cooler. Such a heat exchanger is particularly advantageous to reduce the desublimation surface of the crystallization apparatus since part of the sensible heat can already be removed from the vapor stream before entering the crystallization apparatus.

The direct connection between the crystallization apparatus and the devolatization apparatus has the effect that both devices operate substantially under the same vacuum conditions. That means that no throttling means or vacuum pumps are arranged between the crystallization apparatus and the devolatization apparatus.

It has been found by the inventors, that the viscosity of condensed lactide fraction in a melt crystallization step surprisingly allows a sufficient mass transfer and in turn a sufficient purification of the crystal fraction. Melt crystallization is to be understood a as a crystallization, which is solvent-free. The viscosity of the melt can be up to 100 mPas, whereby the viscosity is preferably lower than 10 mPas, particularly preferred lower than 5 mPas.

According to a preferred embodiment, the method comprises a first step, in which a raw material is processed for the extraction of fermentable polysaccharides. The raw material may stem from corn, sugar plants, cane, potatoes or other sources o fermentable polysaccharides. In a second step a fermentation using suitable bacteria to obtain a raw lactic acid is performed. In a third step the solvent is removed from the mixture. According to a preferred method, the solvent may be removed by evaporation. The solvent can in particular be water. In a fourth step the lactic acid is catalytically dimerized to form a raw lactide. An optional intermediate step can be performed, which includes a pre-polymerization of the lactic acid to a low molecular weight polylactic acid and subsequent depolymerization to form a raw lactide. The lactic acid, which has not been reacted to raw lactide can be drained and be recycled to the apparatus for performing the third step. The heavy residues from the lactide reactor can be recycled to the reactor of any of the second or third steps. A portion of the heavy residues can also be added to the subsequent sixth step, which includes the polymerization of the purified lactide to polylactic acid or can be recycled to the apparatus for performing the third step.

In a fifth step the purification of the lactide is performed to remove foreign substances, which may influence the polymerization in a negative manner and contribute to the coloring as well as the odor of the final product. The separation can either be performed by distillation or by a crystallization process. The unwanted compounds, such as non-reacted lactic acid, other carboxylic acids are contained in the vapor phase, when evaporation is used. These unwanted compounds are present in the non-crystallized residue. The stream of unwanted compounds may be recycled to any of the apparatus of the third or fourth steps.

In a sixth step, a ring opening polymerization for obtaining raw polylactic acid of high molecular weight is obtained. During polymerization the temperature dependent equilibrium between the monomer and the polymer is reached. The raw polylactic acid contains about 4-6 weight % of non-reacted lactide. The monomer content has to be reduced to less than 0.5% in order to obtain the required mechanical properties of the polymer for further processing thereof. Therefore the raw polylactic acid has to be purified.

In a seventh step, the raw polylactic acid is purified to obtain a purified polylactic acid. In this stage, low boiling compounds are removed, which habitually contribute to the coloring and unwanted odors of the final product or may contain additives, which would have an undesired effect on the ring opening polymerization process if recycled. The separation of the low boiling compounds from the raw polylactic acid is achieved by devolatization for example by flash evaporation under vacuum conditions. The evaporated stream contains at least 30% of lactide, which has not been reacted to polylactic acid during the ring opening polymerization according to the sixth step. Furthermore, the evaporated gas phase stream may contain other low boiling compounds, which contribute to the coloring or smell of the final product, both of which are mostly unwanted properties, reaction by-products or additives having any undesired effect on the ring opening polymerization if recycled.

The purification according to the seventh step may be performed in one or more subsequent devolatization stages. The main portion of the lactide contained in the raw polylactic acid stream is retained in the first devolatization stage, which amounts to a major portion of the total of 5%.

In an eighth step, the lactide is purified and recycled from the evaporated gas phase stream of the seventh step by means of crystallization, which can comprise a desublimation, thus a solidification from the gas phase. During this step, the coloring and odor generating compounds or undesired additives are removed such that the purified lactide can be added again to the ring opening polymerization of the sixth step, thereby preventing any accumulation of such coloring and odor generating compounds or acting in detrimental way to the process in the sixth process step.

The lactide content of the purified PLA leaving the devolatization as a product stream is less than 2%. Preferably, the lactide content of the purified PLA is less than 0.5 weight %.

The lactide content of the evaporated gas phase stream at least 30% weight, preferably at least 60%, most preferred at least 90%.

According to a variant of the method according to the invention, the evaporated stream leaving the devolatization is condensed and crystallized from its liquid state. Such a crystallization can be performed without solvent as a layer crystallization in a falling film crystallizing apparatus or a static crystallization apparatus. Alternatively, the crystallization can be performed in a suspension crystallization apparatus, in which the condensed mixture is cooled so far as to form lactide crystals floating freely in the liquid thereby forming a partially crystallized liquid stream. This partially crystallized liquid stream is fed into a wash apparatus, in which the separation of the solid from the liquid residue is performed.

The crystal fraction obtained by any of the crystallization apparatuses mentioned above contains the purified lactide and is melted in the last crystallization stage to be fed back into the ring opening polymerization according to the sixth step. The non-crystallized mother liquor has to be drawn off from the process as a waste stream or it can be at least partly recycled to any of the above-mentioned upstream process steps e.g. 3, 4, 5 as shown in FIG. 2.

According to a variant of the method according to the invention, the crystallization apparatus, in which the lactide crystals are formed is to be connected directly to the devolatization apparatus. The devolatization operates under a lactide partial pressure of less than 20 mbar, preferably less than 10 mbar, particularly preferred less than 5 mbar. The lactide from the evaporated gas phase stream is solidified onto the cooled crystallization surfaces provided by the crystallization equipment forming crystallization layers. The solidified fraction containing purified lactide is melted in a subsequent heating step to be fed back into the ring opening polymerization according to the sixth step. The liquid fraction, which had not been deposited as crystals on the crystallization surfaces, has to be drawn off from the process as a waste stream.

The heating step to melt the crystals on the crystallization surfaces can be preceded by a sweating step. During the sweating step a partial melting of the crystals is performed. Any remainders of unwanted compounds present between the crystals of polycrystalline layers or on the surfaces thereof can be separated and removed from the lactide crystals. Under a polycrystalline layer, a layer is understood which contains a plurality of crystals. Between the crystals of such a polycrystalline layer, impurities can accumulate. These impurities may be disposed of by the sweating step. The liquid fraction generated during the sweating step has to be drawn off from the process as a waste stream.

In a layer crystallization, the polycrystalline layers are formed on heat exchanging surfaces provided by the crystallization apparatus. According to a preferred embodiment the heat exchanging surfaces are plates or tubes through which a cooling medium circulates. A crystallization apparatus having plates as heat exchanging surfaces is also known as a static crystallization apparatus. A crystallization apparatus having tubes as heat exchanging surfaces is also known as a falling film crystallization apparatus.

In order to increase the purity of the lactides generated from the evaporated gas phase stream of the devolatization, the layer crystallization can be performed in a plurality of stages. The molten crystals resulting from the crystallization of the liquefied evaporated gas phase stream can by crystallized in a further crystallization stage, whereby the purity of the crystallization fraction resulting from this second crystallization step is crystallized anew, whereby the purity of the crystals of the second stage is increased. The liquid residue from the second crystallization stage can be fed back together with any liquid fraction from a sweating step to the feed for the first crystallization stage.

It is possible to foresee more than two crystallization stages, whereby the liquid residue from the last crystallization stage can be fed back together with any liquid fraction from a sweating step to the feed of any one of the preceding crystallization stages. The optimum number of crystallization stages depends on the required purity of the lactide.

Furthermore, the crystals generated by solidification from the gas phase can be molten and then be recrystallized for increasing the purity of the lactide.

According to a further variant for increasing the yield of the lactide from the gas evaporation stream, the mother liquor and or liquid from sweating stage can be collected and be recrystallized in order to recover the lactide contained still in the two fractions.

The mother liquor from the first crystallization step, thus the liquefied evaporated gas stream is crystallized to obtain the lactide as crystallized fraction. The content of the lactide in the mother liquor and/or liquid from the sweating stage of this recrystallization stage is lower than in the corresponding fraction of the crystallization of the liquefied evaporated gas stream. The crystallizate of such a recrystallization stage can also be submitted to a sweating step and subsequently melted to be added to the liquefied devolatization fraction. It is possible to employ further recrystallization stages, whereby the content of the lactide in the liquid residue and/or the liquid from the sweating step of a subsequent recrystallization stage is reduced compared to each previous recrystallization stage. Thereby the mother liquor and/or the liquid from the sweating step of a subsequent recrystallization stage are fed into a previous recrystallization stage and the molten crystallizate is fed into a subsequent recrystallization stage. The number of recrystallization stages is determined by a cost optimization over the entire process.

The layer crystallization in the embodiment of a melt crystallization or a solidification from the gas phase, that is a desublimation, are batch processes. Advantageously these steps are performed in one or more crystallization apparatuses, such as a melt crystallization apparatus or a desublimation apparatus. The working sequence of these apparatuses is advantageously staged so as to perform a crystallization or desublimation in one of the apparatuses while performing a sweating or melting in any of the other apparatuses. In such a way, a continuous discharge of the evaporated gas phase stream for crystallization is guaranteed without the need of intermediate buffering.

A notable advantage of the recycle of the lactide from an evaporated gas phase stream from the devolatization apparatus is the use of less complicated equipment and a simpler process as compared to the prior art such us the processes disclosed in U.S. Pat. No. 6,187,901 or U.S. Pat. No. 5,880,254. The crystallization apparatus is of a simple mechanical construction. Furthermore no inert gas streams are required, thus any treatment steps for such an additional inert gas stream are not necessary, which results in substantial cost advantages in favor of the lactide regeneration process according to the invention.

A further object of the invention is to improve the purification of a vaporous biodegradable, intermolecular cyclic diester of an alpha-hydroxy-carboxylic acid and to keep the waste as small as possible and to reduce the equipment to perform the purification.

This object is achieved by a method for the melt layer crystallization of a vaporous biodegradable, intermolecular cyclic diester of an alpha-hydroxy-carboxylic acid of the formula I

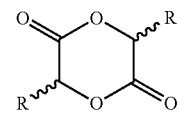

wherein R is chosen from hydrogen or one of a linear or branched aliphatic radical having one to six carbon atoms of a melt stream containing the diester of the formula I.

In particular, the temperature of the melt stream when entering a melt layer crystallization apparatus for performing the melt layer crystallization is adjusted to between 0° C. and 130° C., preferably between 10° C. and 110° C. to crystallize the diester of the formula I when the partial pressure of the diester in the evaporated gas phase stream is not more than 20 mbar, preferably not more than 10 mbar, particularly preferred not more than 5 mbar. The concentration of the diester of the formula I in the melt stream is advantageously adjusted to a minimum of 30 wt. %, preferably a minimum of 40 wt. %, particularly preferred a minimum of 60 wt. %, in particular a minimum of 70 wt. %. According to a preferred embodiment, the melt stream has a water content of less than 10%, in particular less than 5%, most preferred less than 1%. The method is particularly suitable for purification of the diester of the formula I being 3,6-dimethyl-1,4-dioxane-2,5-dione (dilactide), in particular L, L-dilactide.

According to an advantageous embodiment, at least a part of the diester of the formula I originates from an upstream purification device, which can be in particular stem from at least one of a process stage of the preparation of polylactide, the polycondensation of lactic acid, the thermal depolymerisation of oligomers of lactic acid with an average molecular weight of between 500 g/mol and 5,000 g/mol, the rectification of dilactide, the ring-opening polymerization of a dilactide-containing reaction mixture, the vacuum demonomerization of polylactide or copolymers thereof. The upstream purification can involve two or more process stages of the abovementioned processes and/or several of the abovementioned processes simultaneously.

In particular, an alpha-hydroxy-carboxylic acid of the formula I from a alpha-hydroxy-carboxylic acid of the formula II

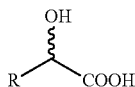

can be used for the preparation of a biodegradable, intermolecular cyclic diester, wherein R is chosen from hydrogen or one of a linear or branched aliphatic radical having one to six carbon atoms. According to a particularly preferred embodiment, the alpha-hydroxy-carboxylic acid of the formula II is lactic acid.

The concentration of the alpha-hydroxy-carboxylic acid of the formula II in the melt stream is advantageously adjusted to a maximum of 20 wt. %, preferably a maximum of 5 wt. %, particularly preferred a maximum of 1 wt. %. If the concentration of the alpha-hydroxy-carboxylic acid in the melt stream can be limited to less than 10 wt. % the lactide obtained by the melt crystallization apparatus can be of a higher purity and this lactide can be fed back into the previous purification step to increase the purity of the end product, thus the polylactic acid. By this measure it is possible to produce a polylactic acid of a high purity and high molecular weight.

If the concentration of the alpha-hydroxy-carboxylic acid in the biodegradable, intermolecular cyclic diester can kept low, it is also possible to control the polymerization and to adjust the physical and chemical properties of the biodegradable, intermolecular cyclic diester according to formula I.

In particular a polylactic acid (PLA), particularly L- or D-polylactic acid (PLLA or PDLA), having a molecular weight of at least 10 000 is obtainable. Advantageously, the molecular weight of the PLA is at least 20 000, particularly advantageous a molecular weight of at least 50 000.

The lactide recovered and recycled according to the method of the invention has a sufficient purity for being re-used in the polymerization process leading to PLA with the above-mentioned desired parameters.

A layer crystallization apparatus according to the invention comprises a vessel, receiving a melt stream containing a biodegradable, intermolecular cyclic diester of an alpha-hydroxy-carboxylic acid according to the formula I,

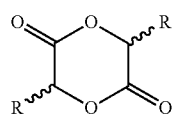

whereby R is chosen from hydrogen or one of a linear or branched aliphatic radical having one to six carbon atoms. The layer crystallization apparatus further comprises a heat exchanger having a heat exchange surface a heat transfer medium for cooling the heat exchange surface and a crystallization surface provided on the heat exchange surface for growing crystals of the diester of formula I.

A polymerization plant for the polymerization of the diester according to formula I comprises a layer crystallization apparatus according to the invention. The polymerization plant can further comprises at least a purification apparatus for the biodegradable, intermolecular cyclic diester according to formula I and/at least one depolymerization reactor arranged upstream of the layer crystallization apparatus.

These and other objects and advantages of the invention will become more apparent from the following detailed description, taken in conjunction with the accompanying drawings wherein.

Figure 1:
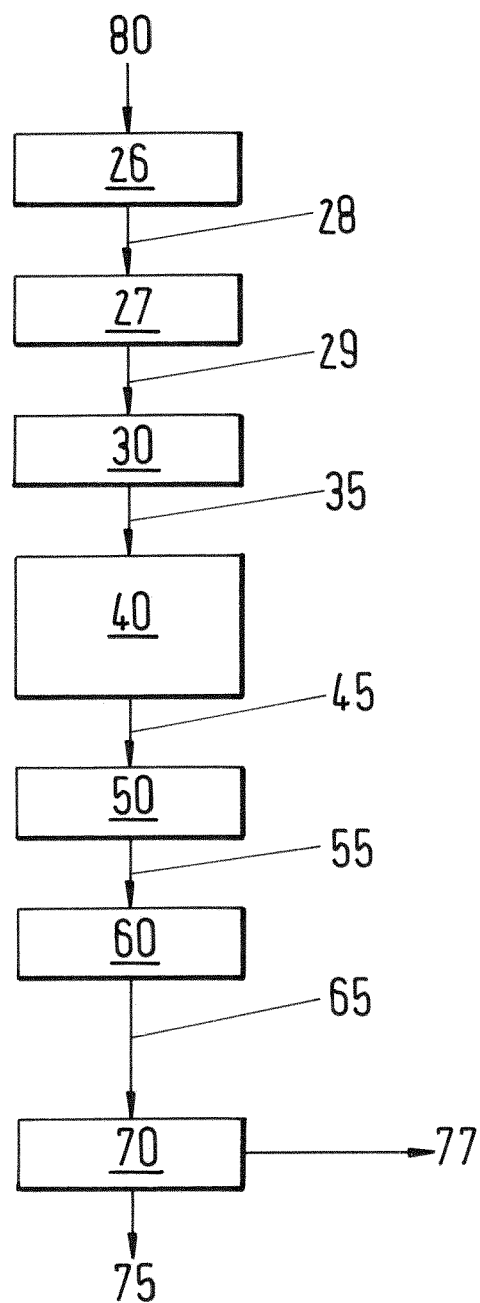
FIG. 1 shows a flow chart of the method according to the invention.
Figure 3:
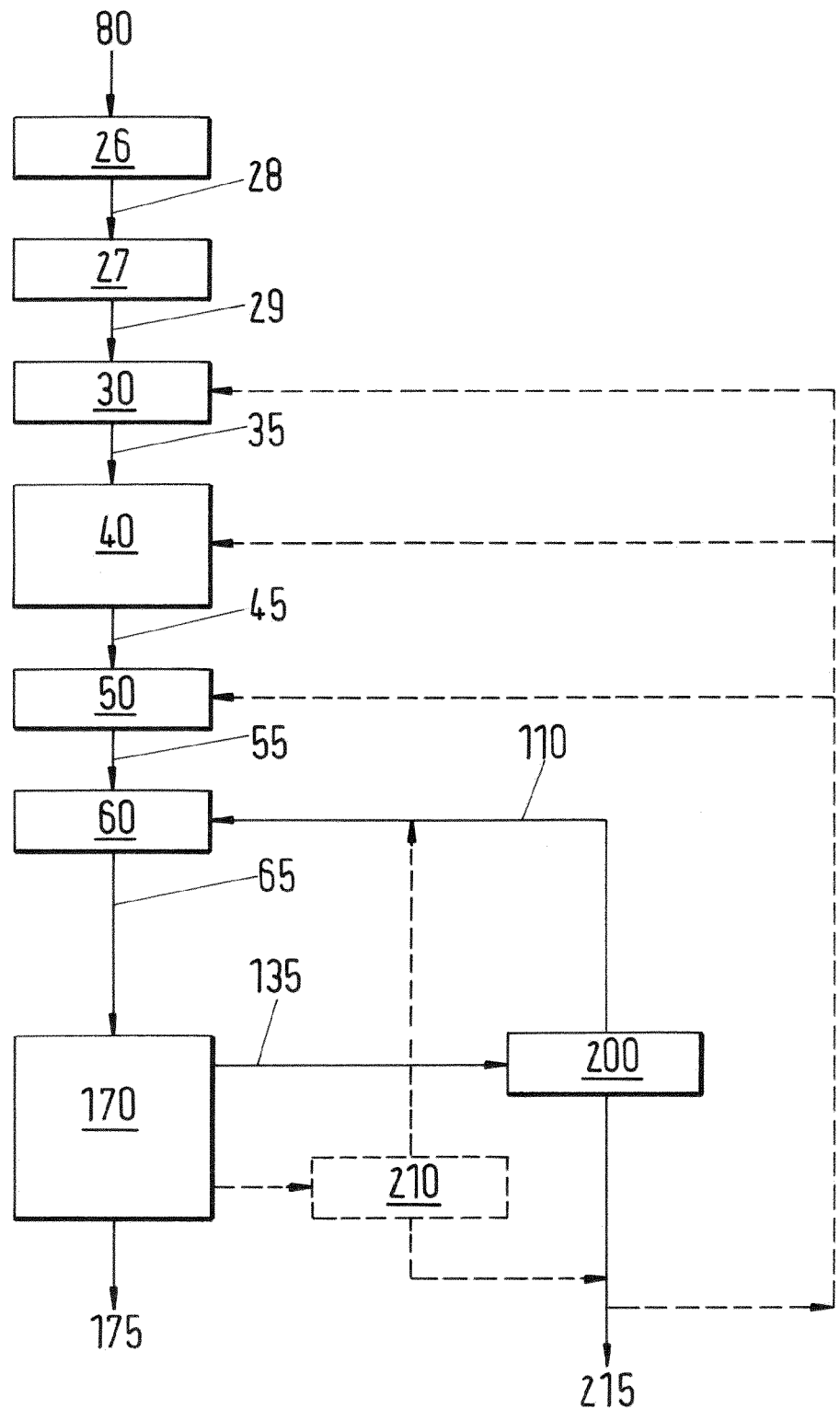
Figure 4:
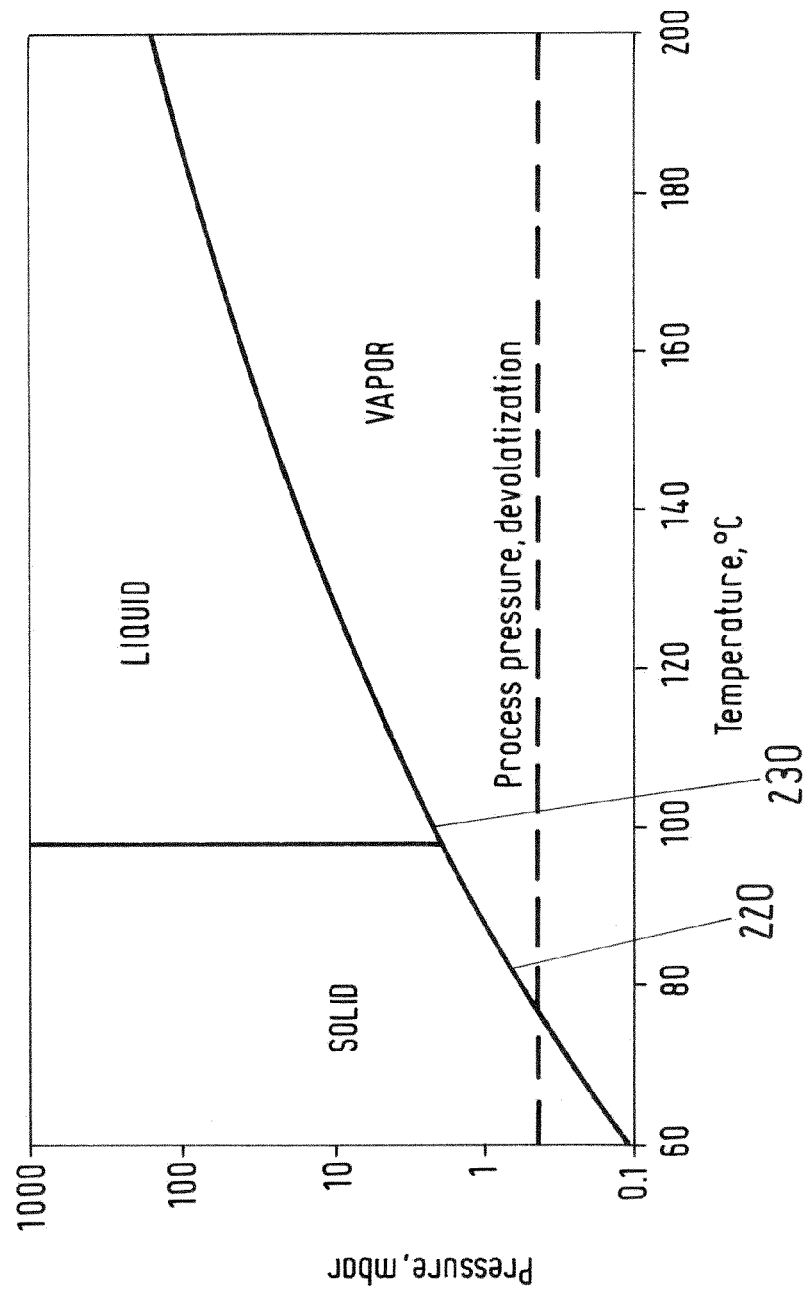
Figure 5:
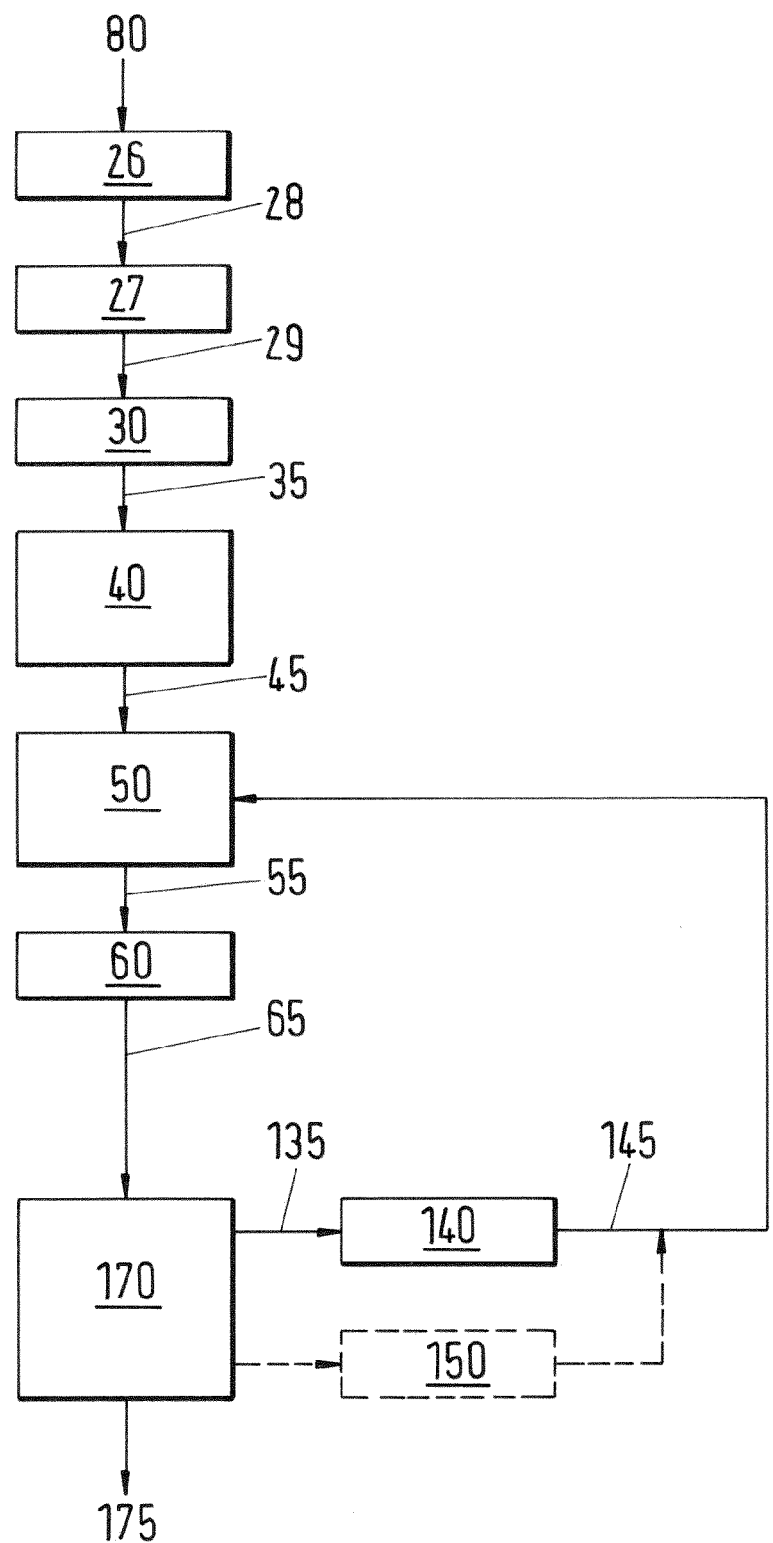
Figure 6:
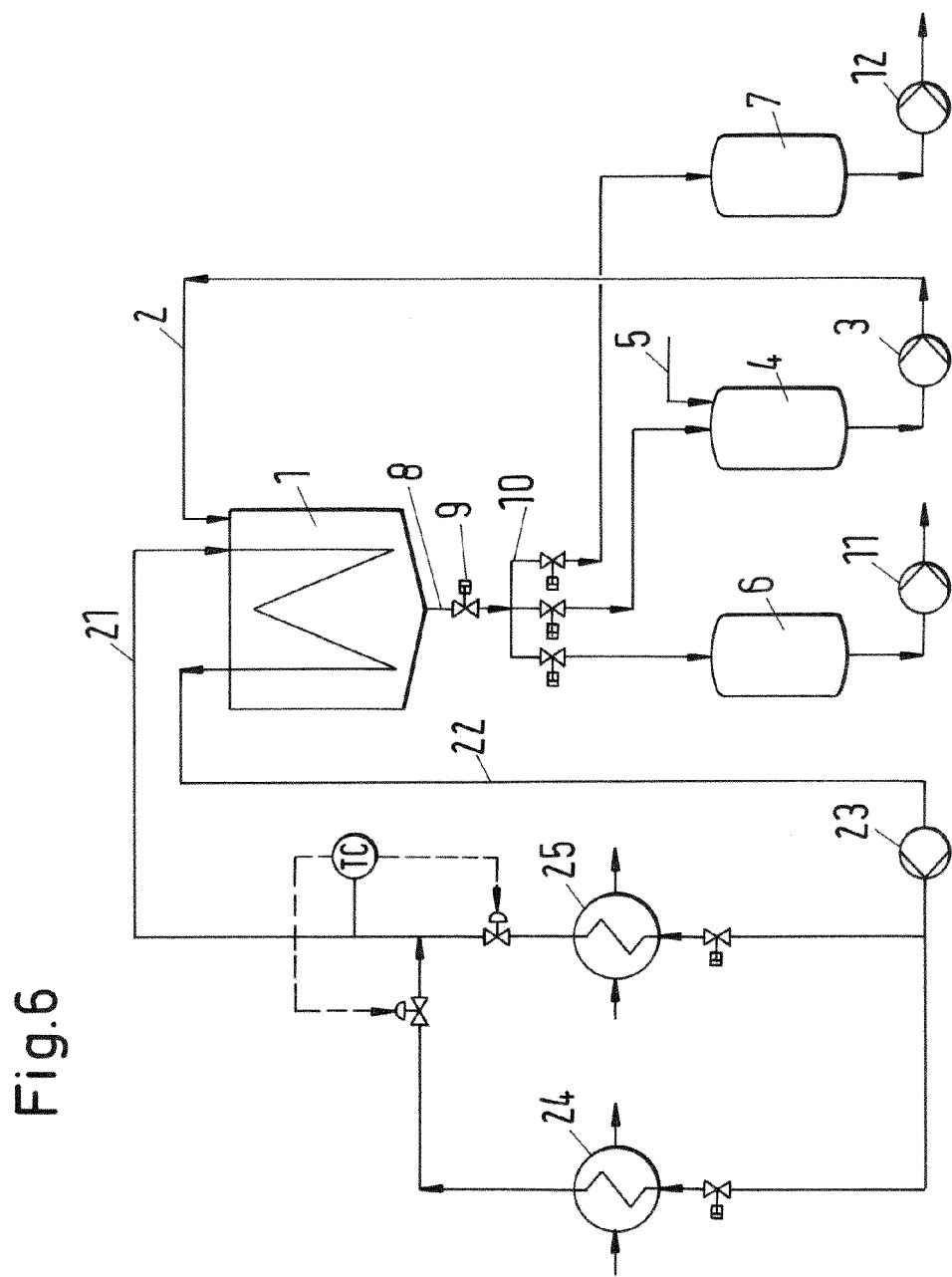
Figure 7:
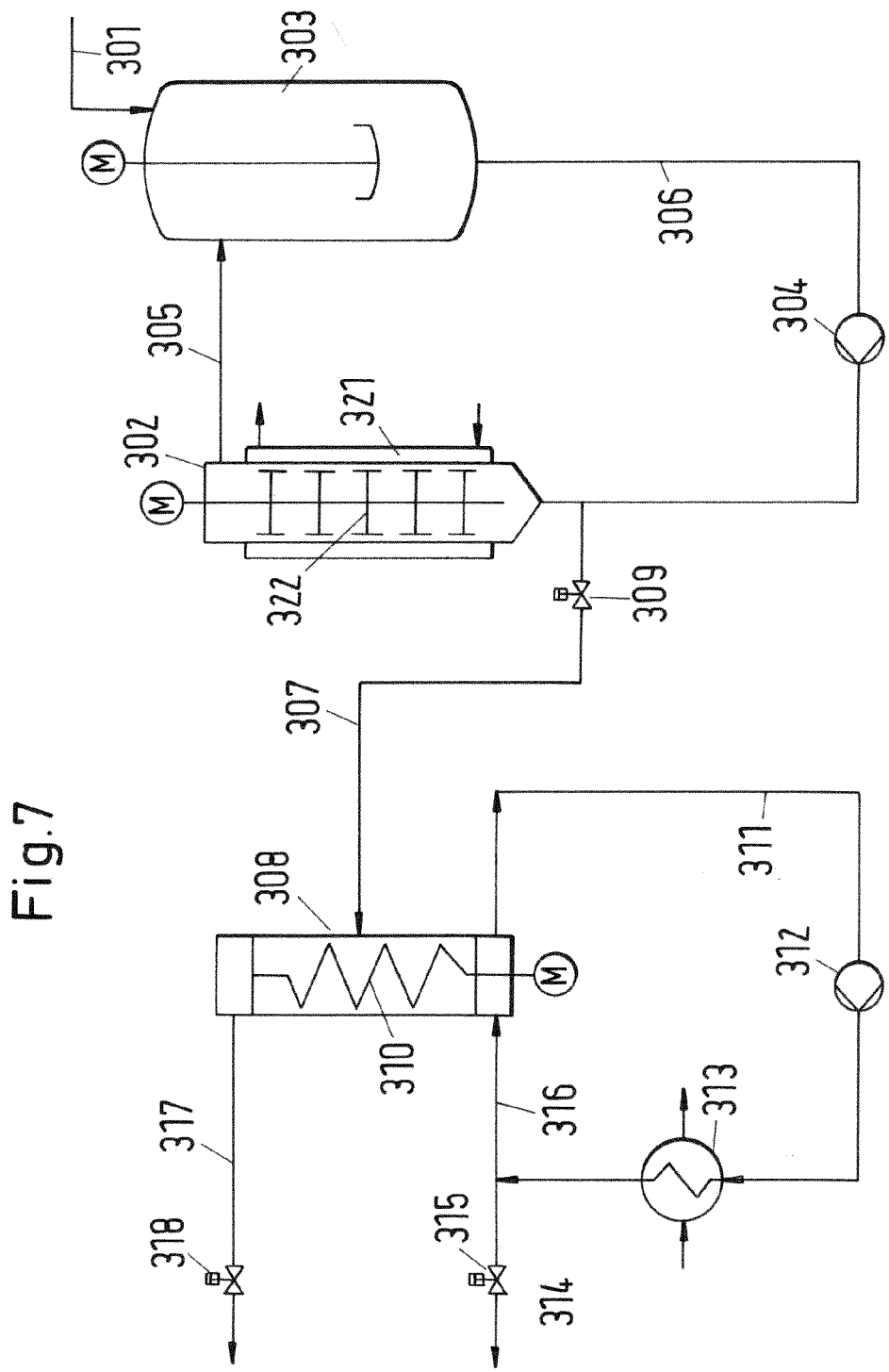
Figure 8:
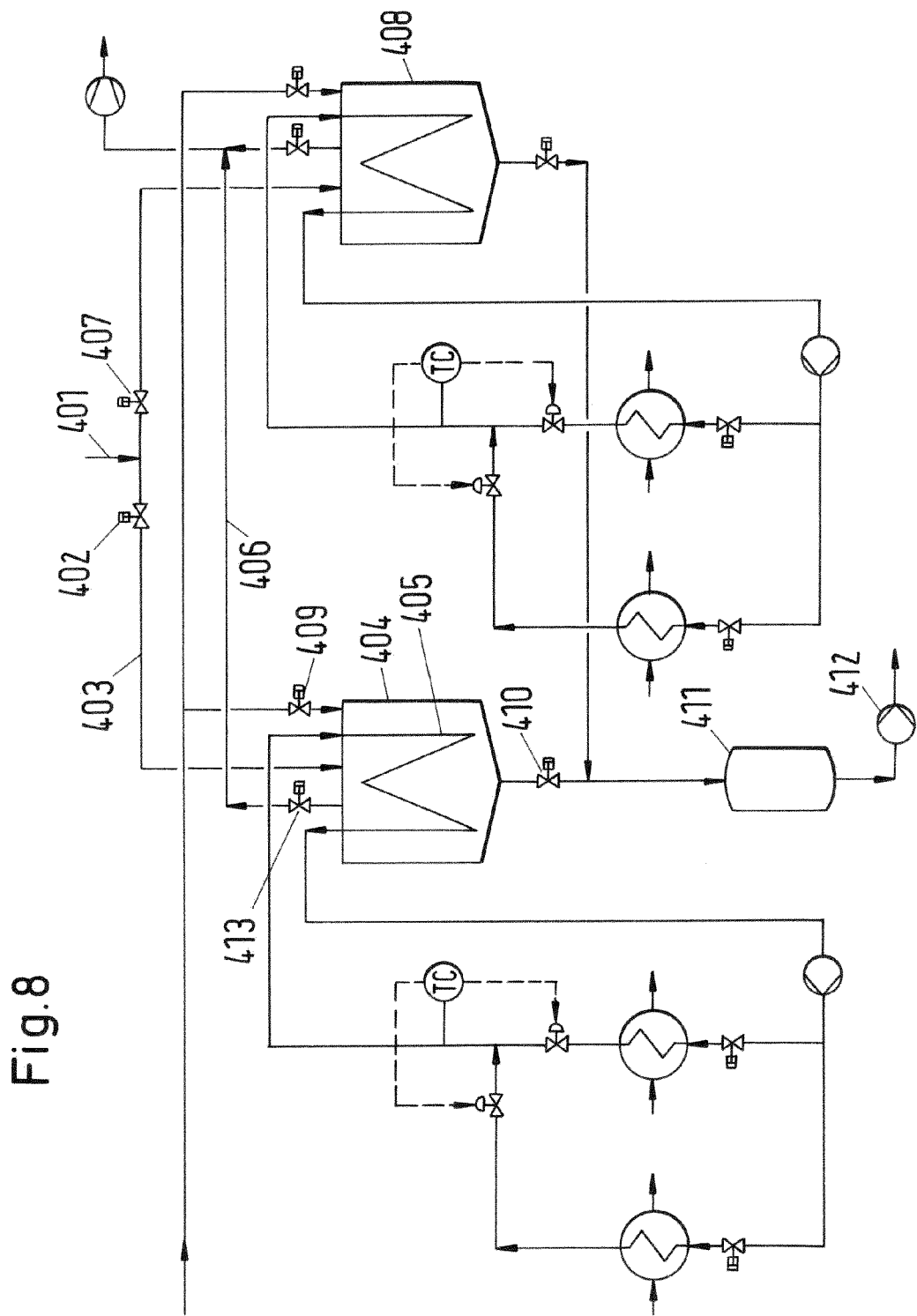
Figure 9:
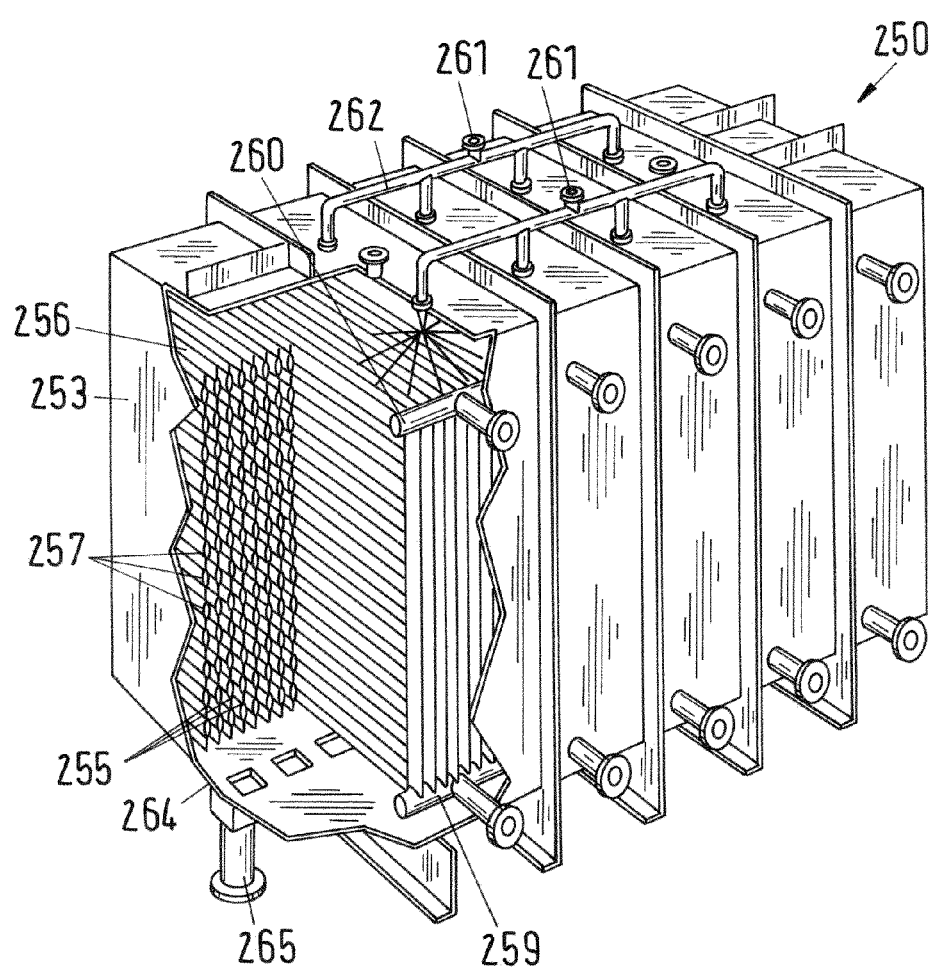
Figure 10:
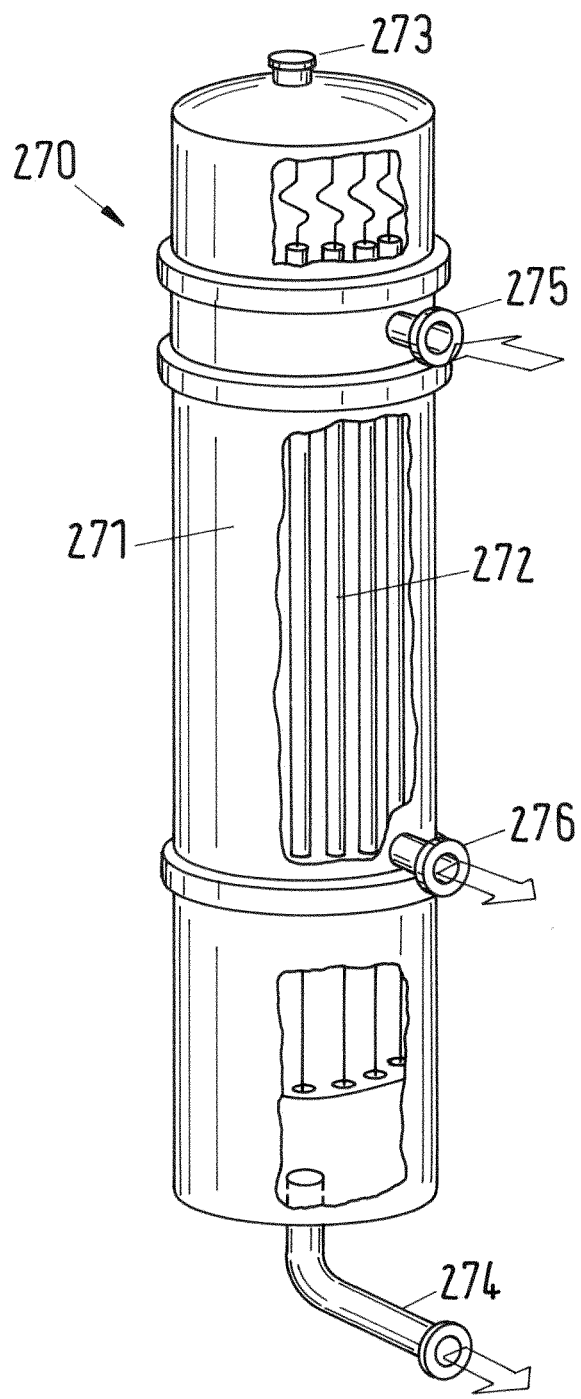

FIG. 3 shows the regeneration of lactide from the evaporated gas phase stream of the devolatization step by means of desublimation FIG. 4 shows a phase diagram of lactide FIG. 5 shows the regeneration of lactide from the evaporated gas phase stream by the raw lactide crystallization step FIG. 6 shows an embodiment of a crystallization plant FIG. 7 shows an embodiment of a suspension crystallization plant FIG. 8 shows an embodiment of a desublimation plant FIG. 9 shows a first embodiment of a layer crystallization device FIG. 10 shows a second embodiment of a layer crystallization device FIG. 1 shows the method for producing PLA from lactide and the ring opening polymerization. The steps in FIG. 1 include a preparation step 26 followed by a fermentation step 27 performed in a fermentation apparatus. During the preparation step 26, a biomass feed 80 is transformed into a raw material stream 28. After the preparation step 26, the raw material stream 28, containing polysaccharides and/or polysaccharides is fed into the fermentation apparatus for performing the fermentation step 27. The fermentation apparatus can be a reactor vessel containing the liquid reaction mixture. If needed, a stirring element may be foreseen to homogenize the reaction mixture while the fermentation reaction is performed. The fermentation may be performed as a batch process or as a continuous process. The product of the fermentation step leaving the fermentation apparatus is a raw lactic acid in solution 29.

As a next step, the solvent has to be removed from the raw lactic acid in a solvent removal step 30 so to obtain a purified lactic acid 35. The solvent can be treated and recycled at least partially to be added during the fermentation step 20. The purified lactic acid is subjected to a pre-polymerization and dimerization step 40 to obtain a raw lactide 45.

As a next step the raw lactide 45 is to be purified in a raw lactide purification step 50. The product of the raw lactide purification step is a pure lactide 55. The pure lactide stream contains at least 85 weight % of lactide. Any lactic acid present in the pure lactide stream is less than 0.2% and any water is present in less than 1%, preferably less than 0.1%. The pure lactide 55 is processed to raw PLA 65 in a ring opening polymerization step 60. The raw PLA 65 can be further purified in a purification step for raw PLA 70 to obtain a pure PLA 75. Any impurities are removed from the purification apparatus as a purge 77.

Figure 2:
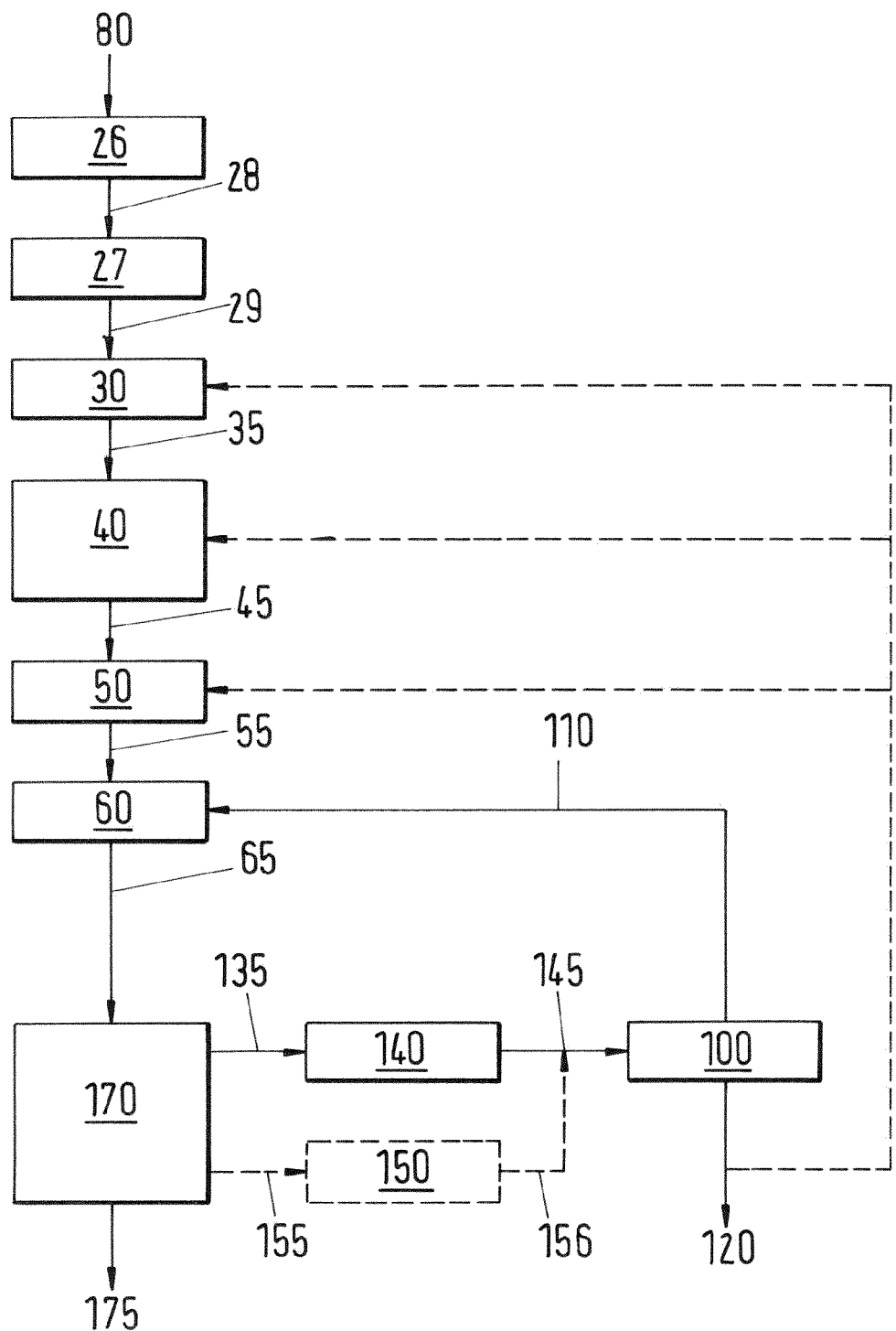
FIG. 2 shows the regeneration of lactide from the evaporated gas phase stream of the devolatization step by means of crystallization.

FIG. 2 shows the regeneration of lactide from the evaporated gas phase stream 135 by means of crystallization. FIG. 2 in particular relates to the treatment of the purge 77 of FIG. 1. In FIG. 2, the steps, which have been already discussed in connection with FIG. 1 are not explained again. These steps carry the same reference numbers and are not explained in further detail. The raw PLA 65 from the ring opening polymerization step 60 is purified in a purification step 170. This purification step 170 is performed as a devolatization in a devolatizer. By this purification step a purified PLA 175 is obtained. In a devolatizer, the low boiling fractions from the raw PLA 65 containing lactide are vaporized under vacuum conditions. Thereby the evaporated gas phase stream 135 is obtained. This evaporated gas phase stream 135 is cooled and condensed in a condensation step 140. The condensate 145 is fed into a crystallization step 100. During the crystallization step a pure lactide stream 110 is obtained, which can be fed into the ring opening polymerization step 60 together with pure lactide stream 55. The purge 120 from the crystallization step 100 is a waste stream, however it is possible to recycle at least a portion thereof to the raw lactide purification step 50, the pre-polymerization and dimerization step 40 or the solvent removal step 30.

As an alternative, the devolatization step can be performed in more than one stage. During each such additional stage an evaporated gas phase stream can be generated. One such additional condensation step 150 is shown in FIG. 2 for an evaporated gas stream 155 from such an additional devolatization step. The condensate 156 of this additional condensation step 150 is fed either into the condensate stream 145 or directly into the crystallization apparatus for performing the crystallization step 100.

FIG. 3 shows a variant of the method as shown in FIG. 2. The condensation step 140, 150 and the crystallization step 100 is substituted by a desublimation step 200. Thus condensation and crystallization occur in the same apparatus due to the fact that the evaporated gas phase stream is solidified directly from the gas phase stream.

A plurality of desublimation steps may alternatively foreseen, in particular if a plurality of devolatization steps is foreseen. An additional desublimation step 210 is shown in FIG. 3 as optional alternative in dotted lines. The purge stream 215 is a waste stream, however it is possible to recycle at least a portion thereof to the raw lactide purification step 50, the pre-polymerization and dimerization step 40 or the solvent removal step 30.

Such a desublimation is possible in a low pressure region. In the phase diagram for the lactide a phase transition from gas phase to solid phase is possible along curve 220. The curve 220 extends from the y-axis, which corresponds to a temperature of 60° C. to the triple point 230. When cooling the lactide at a pressure or partial pressure of less than 2 mbar, a direct transition from the gas phase to the solid phase takes place.

FIG. 5 shows a further variant of the method according to FIG. 2. FIG. 5 shows the regeneration of lactide from the evaporated gas phase stream 135 by means of crystallization. In FIG. 5, the steps which have been already discussed in connection with FIG. 1 or FIG. 2 are not explained again. The steps, by which the same task as in FIG. 1 or FIG. 2 is performed, carry the same reference numbers and are not explained in further detail. The raw PLA 65 from the ring opening polymerization step 60 is purified in a purification step 170. This purification step 170 is performed as a devolatization in a devolatizer. The evaporated gas phase stream 135 containing the low boiling fraction of the devolatization step is cooled and condensed in a condensation step 140. The condensate 145 is fed into the equipment for performing the lactide purification step 50, which can include a crystallization step. A purge stream containing the impurities, which should not be present in the PLA can be drawn off from the lactide purification apparatus to perform the lactide purification step 50.

The devolatization can be performed in more than one devolatizer. The condensation 150 of the evaporated gas phase stream 155 can be performed separately from the condensation 140 of the first devolatization step.

EXAMPLE 1

A solvent free ring opening polymerization to obtain a raw polylactic acid has been performed in two different tests. The following conditions apply to the first and second test of example 1: the raw polylactic acid is fed into a purification apparatus for performing a devolatization. The product of the devolatization is a purified polylactic acid and an evaporated gas phase stream containing light boiling compounds such as lactide. The evaporated gas phase stream from the devolatization has a lactide content of around 98.5% and is liquefied in a condenser and fed into a vessel of a layer crystallization apparatus to be solidified to form a solidified mass. The solidification takes place by crystallizing the lactide on the heat exchanging surfaces of the layer crystallization apparatus. Thereafter the solidified mass is molten after having been transported to the layer crystallization apparatus by heating of the vessel to form a molten mass. Then the molten mass is fed back into the process, that is in the ring opening polymerization apparatus.

The crystallization step for this test has been performed twice as shown in table 1a. During the first crystallization step, the molten mass has been crystallised, the liquid residue has been discharged. Then the solidified mass has been subjected to sweating. The sweating process has been performed in two stages. At the end of each stage, a measurement of the point of solidification has been performed. The point of solidification of a mixture correlates with the purity of the main component in the mixture according to the phase diagram of lactide according to FIG. 4 and consequently allows judging the progress of the purification. The purity of the lactide reached after the first sweating step of the first crystallization step has been 99.5%. A purity of 99.6% after the second sweating step of the second crystallization step has been reached.

For the second test, the analysis for particular impurities, that is Sn ions and free acids, has been performed for all fractions, that is the feed, the residue, the sweating fraction and the solidified mass forming the crystallizate. The results of this second test are shown in table 1b. In this test the sweating step has been performed only once.

In a third test, the crystallizate of the second test has been molten again and crystallized. In this test, only the residue has been discharged and a sweating step has not been performed. The results of this crystallization are summarized in table 2.

The Sn ions stem from the catalyst. Under free acids, it is intended any acids which would act as a chain stopper during polymerization. Moreover, the coloring and odors of the feed and the crystallizate obtained by each of the sweating stages are compared to each other in table 1a and table 1b.

TABLE 1a

Results of the crystallization of the evaporated gas stream from devolatization according to the first test

| Fraction | Mass, g | Solidification point, ° C. | Coloring | Odor |
|---|---|---|---|---|
| Feed | 3560 | 95.76 | yellowish | strong, "atypical" |
| Residue | 940 | 92.36 | — | — |
| Sweating Fraction 1 | 418 | 95.95 | — | — |
| Sweating Fraction 2 | 314 | 96.56 | — | — |
| Crystallizate | 1888 | 97.08 | nearly colorless | weak, "typical" |

TABLE 1b

Results of the crystallization of the evaporated gas stream from devolatization according to the second test:

| Fraction | Mass, g | Solidification point, ° C. | Sn, ppm | Free Acid, mmol/kg | Coloring | Odor |
|---|---|---|---|---|---|---|
| Feed | 5200 | 96.07 | 13 | 72 | yellowish | strong, "atypical" |
| Residue | 808 | 90.50 | 52 | 274 | — | — |
| Sweating Fraction | 875 | 96.01 | 14 | 71.9 | — | — |
| Crystallizate | 3517 | 97.01 | 3 | 22.2 | nearly colorless | weak, "typical" |

TABLE 2

Results of the repeated crystallization:

| Fraction | Mass, g | Solidification Point, ° C. | Sn, ppm | Free Acid, mmol/kg | Coloring | Odor |
|---|---|---|---|---|---|---|
| Feed | 3240 | 97.01 | 3 | 22.2 | nearly colorless | weak, "typical" |
| Residue | 1367 | 96.47 | 6 | 54.4 | — | — |
| Crystallizate | 1873 | 97.15 | <2 | 7 | colorless | weak, "typical" |

EXAMPLE 2

Desublimation

In this test the separation effect of the desublimation the purity of the lactide has been checked.

The evaporated gas phase stream from the ring opening polymerization, which was also used for the tests of example 1, has been fed into a tube having an inner diameter of 50 mm and a length of 3 m, in which the lactide has been desublimised, thus solidified directly from the gas phase to form a crystallizate on the heat exchanging surfaces of the layer crystallization apparatus, which has been employed for the tests according to example 1. The residue has been fed back into the main process stream thus a subsequent devolatization stage.

A solid layer of a thickness between 10 and 15 mm has been produced and deposited on the inner surface of the tube. When the desublimation has been finished, a portion of the deposited solid layer has been discharged from the tube and molten to form a molten mass. The solidification point of this molten mass has been determined. The solidification point has been measured and was 96.97° C. The solidified molten mass was nearly colourless and had only a weak odour.

Each of the test results of the first and second examples show that the purification of the lactide of the evaporated gas stream can be sufficiently close to the melting point of pure lactide. The purity of the lactide obtained by desublimation according to this example was about 99.5%. For L-lactide the melting point is at 97.7° C.

The tests have been conducted in a lab test static crystallizer with the below-mentioned design details. A static crystallizer is a special embodiment of a layer crystallization apparatus in which the melt is not subjected to any forced convection during the crystallization. The test static crystallizer consists of a vertically arranged jacketed 80 mm diameter tube with a length of 1,200 mm and having a rated volume of 6 l. The tube has a tightly closing lid at the top allowing filling the input melt into the tube and to close the tube tightly during the crystallization. At the bottom, the tube diameter is reduced to 20 mm and there is an outlet valve placed directly below the passage of reduced diameter. The valve allows the liquid fractions be drained out of the tube by gravity. In the jacket of the tube, a heat transfer medium is circulated that supplies the cooling or heating energies for the crystallization and subsequent sweating and melting steps. The heat transfer medium is either heated or cooled in a commercial thermostat apparatus with time-programmable temperature profiles.

After filling the input melt mass into the crystallizer tube, the filling aperture is closed. The heat transfer medium temperature is then dropped to a value for start of crystallization and then it is decreased according to programmed temperature/time profile to the final value of crystallization. During this cooling, the crystals nucleate and start growing upon the inside wall of the crystallization tube. After termination of the crystallization, the non-crystallized residue is drained to a receiver container by opening the drain valve at the bottom of the tube. The sweating fraction is collected to different containers, if required in several cuts. After the sweating has been finished, the drain valve is closed, and the remaining crystals are molten and drained out of the crystallizer tube to the corresponding container by again opening the drain valve.

When operated the two first stages have been subjected to the following operating conditions: The crystallizer tube has been pre-cooled to 95° C. for the start of the crystallization. The temperature of the heat transfer medium has been gradually decreased to the final value of 90° C. within six hours thereafter. During this period the crystallization of the lactide on the heat exchange surfaces has been performed. The melt has been kept in the vessel of the crystallization apparatus to allow for the growth of the crystals. When the crystallization has been completed, the drain valve has been opened to discharge the liquid residue, thus the mother liquor.

After opening the drain valve for the residue drainage, the temperature of the heat transfer medium has been gradually increased to 98° C. to perform a sweating step. The sweating step has lasted for five hours. After having completed the sweating step the liquid residue has again been discharged by opening the drain valve.

Subsequently the crystallizate has to be removed from the heat exchanging surfaces of the layer crystallization apparatus. The melting has been performed at a temperature of 120° C. During the melting the drain valve is held closed and opened only after completion of the melting step for discharging the melt from the crystallization vessel.

During the second stage, the crystallizer tube was pre-cooled to 96° C. for the start of the crystallization. The temperature of the heat transfer medium was then gradually decreased to the final value of 92° C. within six hours. After opening the drain valve for the residue drainage, the temperature of the heat transfer medium was gradually increased to 98° C. at the end of sweating. The sweating lasted five hours. The melting performed at a temperature of 120° C.

Solvent-free melt crystallization is used in a commercial scale. A crystallization apparatus comprising falling film crystallizers as described e.g. in U.S. Pat. No. 3,621,664 is commercialized by Sulzer Chemtech Ltd. Switzerland.

Alternatively the crystallization apparatus can comprise static crystallizers as described in e.g. EP0728508 (A1); EP1092459 (B1); EP0891798 (B1) and is commercialized by e.g. Litwin, France; Sulzer Chemtech Ltd., Switzerland. The static crystallizer essentially consists of a tank, in which the crystallized melt is filled in and of cooling surfaces being cooled/heated from the inside by a heat transfer medium. The heat transfer medium circulate in a vertical plate bundle as shown in FIG. 9 or a tube bundle as shown in FIG. 10. The crystals grow on the external walls of these heat exchanging surfaces.

Alternatively the crystallization apparatus can comprise a suspension crystallization apparatus as described e.g. in U.S. Pat. No. 6,719,954 B2; EP 1 245 951 A1; U.S. Pat. No. 6,241,954 B1; U.S. Pat. No. 6,467,305 B1; U.S. Pat. No. 7,179,435 B2; US 2010099893 (A1) and is commercialized by GEA Messo PT, Germany and Sulzer Chemtech Ltd. Switzerland. In such a suspension crystallization apparatus small crystals are created, which grow in suspension in a growth vessel. The growth vessel and the suspension crystallization apparatus may be merged together as one unit. The slurry is then conveyed to a wash column where the crystals are washed by counter currently flowing, partly returned molten crystal fraction and the wash liquid, being loaded with the non-desired components is rejected as residue. The residue of as first suspension crystallization apparatus may be collected and recrystallized and washed again in a second suspension crystallization apparatus of similar configuration so as to recover any lactide from the residue of the first assembly.

In FIG. 6, a melt layer crystallization apparatus comprising a static plate bundle crystallizer 1 is shown. The configuration of such a crystallizer can have the same or corresponding elements to the crystallization apparatus as shown in FIG. 9. The crystallizer 1 is loaded with a batch of molten mass to be crystallized by a line 2 by means of a pump 3 from the lactide feed vessel 4. The feed is coming to the feed vessel by a feed line 5. This feed can be either a gaseous stream or a melt stream. In particular, the feed may be an evaporated gas phase stream from a devolatization unit (70, 170) as shown in FIG. 1, 2, 3, 5.

The residue of the crystallizer 1 as well as the sweat fraction and the molten crystal fraction are drained to the appropriate vessels 6, 4 and 7, respectively, by outlet line 8 and drain valve 9. A header 10 with necessary valves allows to direct the particular fractions being drained to the appropriate vessels. The header has the function of a liquid distributor. The residue is collected in vessel 6. The molten crystal fraction, which contains the purified lactide is drained to vessel 7. The residue and purified lactide can be transferred to their destinations by the transfer pumps 11 and 12. The sweat fraction can be collected in vessel 6 and discharged in the same way as the residue or it can be collected in vessel 4 for being recycled to the crystallizer 1 by line 2. The plate bundle as shown in FIG. 9 is cooled and heated by heat transfer medium coming by line 21 and leaving the bundle by line 22. The circulation pump 23 allows the heat transfer medium be continuously circulated in the energy system. The cooling and heating energies are supplied via both heat exchangers 24 and 25. The here shown heat exchangers represent only one, simple possibility of the energy supply to the crystallization system. There are other solutions possible, like systems with energy buffer vessels and other energy supply systems being well known to a person skilled in the art from the industrial practice.

In the embodiment according to FIG. 7, the liquefied lactide from the devolatization is fed continuously via line 301 into the crystallization section of the melt suspension crystallization apparatus. The melt suspension crystallization apparatus comprises a crystallizer and/or scraper unit 302 and a vessel 303 for growing crystals. A transfer line 305 leads from the crystallizer 302 to the vessel 303, a transfer line 306 from the vessel 303 to the crystallizer 302. A circulation pump 304 may be arranged in the transfer line 306, which allows the slurry to be circulated between the crystallizer 302 and the vessel 303. The crystallizer and/or scraper unit has a cooling jacket 321 for cooling the crystallizer unit walls. Crystal nuclei on the internal wall are formed on the inner wall surfaces of the crystallizer 302. The crystal nuclei are then scraped continuously from the internal wall surfaces by a scraper element 322. The crystal nuclei are allowed to grow while being suspended in the melt, which is a lactide melt in accordance with the preferred application.

In an alternative version, both devices, the crystallizer 302 and the vessel 303 may be combined into one common unit. The lactide feed may also be directed to the crystallizer 302, or to one of the circulation line 305 or transfer line 306 instead of the vessel 303. The design details of commercially available melt suspension crystallization devices are known to a person skilled in the art.

A part stream of the slurry is split from the circulation line 306 to line 307 feeding to the wash column 308. The flow rate of this part stream is controlled by a valve 309. The flow rate is essentially the same as the flow rate of the feed of line 301. In the wash column 308, the crystals contained in the slurry are forced to move towards one head of the wash column and the residual melt moves towards the opposite end. The crystals are moved by a mechanical element 310 like screw conveyor or by a piston with a sieve-shaped head, which repeatedly forces the crystals in one direction allowing the melt to pass in the opposite direction. In another type of commercially available wash column 308, the required crystal and melt flow patterns are established by appropriate design of vessel internals in such a way that no movable parts are needed.

The crystal slurry is directed by the mechanical element 310 to a column end, in this example the bottom end or sump and then discharged to the circulation loop 311. A forced circulation of the crystal slurry is maintained by the circulation pump 312. The crystal slurry flows then through the melter 313, in which the crystals are molten to from a molten mass. One part of that molten mass is continuously discharged via the discharge line 314 and the control valve 315. This part is in the preferred application in a polymerization plant for the production of polylactic acid the purified lactide that is then returned to the polymerization reactor or the devolatization. The remaining part flows via return line 316 back to the wash column. This part is used for maintaining the countercurrent flow of crystals and melt within the wash column. At the other end of the wash column, here the column head, the residual melt is taken out of the column via line 317 and valve 318. This residual melt is the purge stream.

In the embodiment according to FIG. 8, the lactide vapor comes via the supply line 401 from the devolatization stage via opened valve 402 and the branch line 403 to the solidification device 404 where is solidifies upon the cooled surfaces 405. The solidification device can be for example at least one of a desublimation unit or a crystallizer. The non-solidified residual vapor can flow via line 406 back to the main process stream, e.g. to the second devolatization stage or be discarded. The heat exchange system is similar to the one as disclosed in FIG. 6 and is not further described here. Reference is made to the description of FIG. 6.

After a portion of the gaseous stream has solidified on in the heat exchanging surfaces of the solidification device 404, the valve 402 closes and the valve 407 opens to direct the vapor to the second solidification device 408 in which the solidification of the vapor is performed. The second solidification device essentially works in the same manner as the solidification device 404.

The solidification device 404 is pressurized by allowing an inert gas, e.g. nitrogen to flow in via valve 409 to increase the working pressure for melting the solidified mass. This solidified mass contains according to the preferred application for the purification of lactides the lactide fraction and is the crystallizate. The heat exchange surfaces are now heated by a heat transfer medium to melt the solidified mass to form a molten mass. The molten mass, in particular the molten lactide is dumped via valve 410 to the collecting vessel 411 from where it can be conveyed by pump 412 to the polymerization or devolatization stages.

After having molten the solidified mass, the drain valve 410 closes and the solidification device 404 is evacuated by valve 413 and line 406 before starting the subsequent solidification.

There are minimum two solidification devices necessary to assure continuous lactide vapor reception, however the number of such devices can be higher and is not limited.

If no subsequent devolatization stage is foreseen, the residue is a waste stream which consequently is to be treated in a waste treatment process. Optionally a sweating step may be foreseen. The heat exchange surface may be advantageously formed as a tube, which is disposed with a cooling mantle. If the solidification device is configured as a falling film crystallization apparatus, it may be configured as shown in FIG. 10. By means of the cooling mantle, the temperature generated on the inner surface of the tube is kept below the sublimation point for the given partial pressure of the vapour to be desublimised, in particular the lactide.

FIG. 9 shows an embodiment of a layer crystallization apparatus. The crystallization apparatus 250 has a container 253 for the reception of the melt which contains the lactide and the impurities to be removed from the lactide, that is the product of the devolatization namely an evaporated gas phase stream or a melt stream thereof. A plurality of wall elements 255 are arranged in this container 253 whereby the wall elements are spaced apart from one another. The wall elements 255 contain closed channels 257 for the circulation of a fluid heat exchange medium. These wall elements are also called plate bundles. Each wall element 255 is selectively heatable or coolable by circulation of the temperature fluid heat exchange medium in the interior of the closed channels 257. The closed channels 257 open into an inlet tank 259 and an outlet tank 260, which serve for the distribution of the fluid heat exchange medium to the Individual channels 257 or for the reception of fluid heat exchange medium from the individual channels.

The intermediate spaces 256 between the wall elements 255 are filled in operation with the melt which contains the lactide to be purified. The melt is distributed over the totality of the wall elements via inflows 261 which open into inflow distribution elements 262 so that the wall elements 255 are surrounded all over by melt. After the filling of the crystallization apparatus 250 with melt, fluid heat exchange medium is conducted as coolant through the channels 257, whereby the wall elements 255 are cooled. The melt crystallizes at the wall elements 255 to a crystallization layer whose thickness increases continuously. Due to the different melting points of the individual lactide and the impurities in the melt, the crystallizate layer contains a higher portion of high-melting lactide. The solid lactide is deposited from the start at the crystallization surfaces of the wall elements 255, which means that it is therefore concentrated in the crystallizate layer. If the melt is cooled further, impurities with somewhat lower melting points may also start to crystallize.

A larger portion of the impurities remains in the liquid phase and is let out via outflows which are located in the base region 264 of the crystallization device 250. The liquid phase is also called the mother liquor. The impurities melting at a lower temperature than the lactide are concentrated in the mother liquor. The mother liquor in this case contains a waste product.

The wall elements 255 are heated again in the second phase of the crystallization. During this second phase, also a partial melting of the crystallizate layer, the so-called sweat phase, may take place. A fraction lactide containing still some impurities resulting from inclusions of mother liquor between the crystal surfaces during crystal growth can be selectively separated during the sweat phase. The crystallizate layer substantially remains connected to the wall elements in the sweat phase; only individual melt drops are drawn off. The low-melting impurities, which have just been freed by the partial melting of the crystals, art concentrated in these first drops. A very selective separation of impurities is thus possible in the sweat phase. The temperature on the surface of the wall elements 255 preferably increases continuously during the sweat phase. In this case, a plurality of fractions can also be drawn off during the sweat phase.

In the third phase, the melting off of the crystallizate layer takes place, that is the removal of the crystallizate from the wall elements 255. For this purpose, the channels 257 in the wall elements 255 are contacted with fluid heat exchange medium which is used as a fluid heating medium.

FIG. 10 shows a falling film crystallization apparatus 270. The falling film crystallization apparatus 270 comprises a container 271 containing plurality of tubes forming a tube bundle 272. The container receives the lactide from the devolatization which is fed into the container as an evaporated gas phase stream or a melt stream. The feed stream enters the crystallization apparatus via inlet tube 273. The tubes of the tube bundle 272 are hollow so as to form a passage for a heat exchange fluid. The heat exchange fluid enters the tube bundle via an inlet conduit 275 and leaves the tube bundle via an outlet conduit 276. The inlet conduit opens into a fluid distribution element being in fluid connection with the passages of the tubes of the tube bundle. The passages of the tubes are received in a fluid collection element being in fluid connection with the outlet conduit 276.

The heat exchange fluid can be a heating fluid or a cooling fluid, depending on the mode of operation of the crystallization apparatus. In the crystallization mode, a cooling fluid is circulated in the tubes, thus lowering the temperature of the outer surfaces of the tube with respect to the feed temperature. The temperature is lowered so as to crystallize the compounds having the highest melting points. The liquid fraction, which is not crystallized, thus the mother liquor, leaves the container in the sump, when the crystallization apparatus is in crystallization mode.

Under crystallization mode it is intended the performing of the crystallization step. Both of the crystallization apparatuses of FIG. 9 and FIG. 10 are designed for a batch operation. That means that after the crystallization step is performed, a melting step is performed to melt the crystal fraction and drain it to the sump from which it is discharged by the discharge tube 274. The crystal fraction is deposited during the crystallization mode onto the external surfaces of the tubes of the tube bundle.

The falling film crystallization allows for a faster crystallization than the melt crystallization apparatus using wall elements in the form of plate bundles.

What is claimed is:

1. An apparatus for preparing polylactic acid, comprising:
   a polymerization reactor adapted for performing a ring opening polymerization to obtain a raw polylactic acid having a Mw of at least 20,000 g/mol,
   a devolatization apparatus adapted for separating low boiling compounds comprising lactide and impurities from the raw polylactic acid having a Mw of at least 20,000 g/mol,
   a crystallization apparatus for purifying lactide from the low boiling compounds separated in the devolatization apparatus and removing impurities by means of a desublimation and a crystallization in the same crystallization apparatus, and
   a recycle line connecting the crystallization apparatus and the polymerization reactor for recycling purified lactide from the crystallization apparatus back into the polymerization reactor
   wherein:
      lactide and a raw polylactic acid having a Mw of at least 20,000 g/mol are present in the polymerization reactor,
      a ring opening polymerization reaction of lactide to form polylactic acid having a Mw of at least 20,000 g/mol is occurring within the polymerization reactor, and
      purified lactide from the crystallization apparatus is present in the recycle line.

2. A method to prepare a polylactic acid comprising providing the apparatus of claim 1 and further comprising the steps of:
   (i) performing a ring opening polymerization in the polymerization reactor using a catalyst and either a catalyst killer compound or an endcapping additive to obtain a raw polylactic acid of MW greater than 20,000 g/mol,
   (ii) purifying the raw polylactic acid in the devolatization apparatus by removing and separating low boiling compounds comprising lactide and impurities from the raw polylactic acid by devolatization of the low boiling compounds as a gas phase stream,
   (iii) purifying the lactide from the devolatization and removing the impurities from the gas phase stream of evaporated low boiling compounds in the crystallization apparatus by means of crystallization by desublimation from the gas phase,
   wherein the lactide is purified and the removed impurities include a catalyst residue and a compound containing at least one hydroxyl group such that the purified lactide is then polymerized by feeding it back into the ring opening polymerization through the recycle line.

3. The method of claim 2, wherein the desublimation occurs on a cooled surface.

4. The method of claim 2, wherein an apparatus for the crystallization and an apparatus for the devolatization operate substantially under a same vacuum condition.

5. The method of claim 2, wherein the desublimation and the crystallization occur in a same apparatus.

6. The method of claim 4, wherein the apparatus for the crystallization has no inert gas stream.

7. The method of claim 2, wherein the evaporated gas phase stream from the devolatization contains at least 30% of lactide, preferably at least 60%, most preferred at least 90%.

8. The method of claim 2, wherein the lactide is first subjected to a sweating step, followed by a melting step, prior to feeding it back into the ring opening polymerization.

9. The method of claim 2, wherein the devolatization operates under a lactide partial pressure of less than 20 mbar, preferably less than 10 mbar, particularly preferred less than 5 mbar.

10. The method of claim 2, wherein the removed impurities include either an organometallic compound or a carboxylic acid.

11. The method of claim 2, wherein at least a portion of a purge stream from the crystallization is recycled to a raw lactide purification step, a pre-polymerization and dimerization step, or a solvent removal step in the production of a purified lactide.

12. The method of claim 8, wherein a liquid from the sweating step is collected and recrystallized in order to recover the lactide.

13. The apparatus of claim 1, wherein no throttling means or vacuum pumps are arranged between the crystallization apparatus and the devolatization apparatus.

14. The apparatus of claim 1, wherein a heat exchanger is arranged between the devolatization apparatus and the crystallization apparatus.

15. The apparatus of claim 1, wherein the crystallization apparatus has heat exchanging surfaces for the solidification of a gaseous stream.

* * * * *